(12) United States Patent
Tsunedomi et al.

(10) Patent No.: US 11,384,385 B2
(45) Date of Patent: Jul. 12, 2022

(54) METHOD FOR PREDICTING THERAPEUTIC EFFECTS OF IRINOTECAN, AND KIT FOR SAME

(71) Applicants: Yamaguchi University, Yamaguchi (JP); Toyo Kohan Co., Ltd., Tokyo (JP)

(72) Inventors: Ryouichi Tsunedomi, Ube (JP); Shoichi Hazama, Ube (JP); Hiroaki Nagano, Ube (JP)

(73) Assignees: Yamaguchi University, Yamaguchi (JP); Toyo Kohan Co., Ltd., Tokyo (JP)

( * ) Notice: Subject to any disclaimer, the term of this patent is extended or adjusted under 35 U.S.C. 154(b) by 41 days.

(21) Appl. No.: 16/624,469

(22) PCT Filed: Jun. 22, 2018

(86) PCT No.: PCT/JP2018/023773
§ 371 (c)(1),
(2) Date: Dec. 19, 2019

(87) PCT Pub. No.: WO2018/235937
PCT Pub. Date: Dec. 27, 2018

(65) Prior Publication Data
US 2020/0115740 A1  Apr. 16, 2020

(30) Foreign Application Priority Data

Jun. 22, 2017  (JP) ............... JP2017-122569

(51) Int. Cl.
*C12Q 1/6827* (2018.01)
*C12Q 1/6876* (2018.01)

(52) U.S. Cl.
CPC ......... *C12Q 1/6827* (2013.01); *C12Q 1/6876* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| 2008/0153093 A1 | 6/2008 | Okamura et al. |
| 2018/0237833 A1 | 8/2018 | Oka et al. |

FOREIGN PATENT DOCUMENTS

| JP | 2008-72913 | 4/2008 |
| WO | 2010/025952 | 3/2010 |
| WO | 2016/132736 | 8/2016 |

OTHER PUBLICATIONS

Han (The Pharmacogenomics Journal 2013 vol. 13 pp. 417-422).*
Sotos et al. Statistics Education Research Journal 2009, Nov. 8(2):33-55.*
Terwilliger and Hiekkalinna European Journal of Human Genetics (2006) 14, 426-437. doi:10.1038/sj.ejhg.5201583; published online Feb. 15, 2006.*
Langdahl (Journal of Bone and Mineral Research 2000 vol. 15, No. 3, pp. 402-414).*
Wall (Nature Reviews Genetics (2003) vol. 4, pp. 587-597).*
Andiappan (BMC Genetics. 2010. 11: 36).*
Zill et al.Molecular Psychiatry (2004) 9, 1030-1036.*
Han (Journal of Clinical Oncology 30, No. 15_suppl May 20, 2012 p. 7089).*
International Search Report based on co-pending PCT Application No. PCT/JP2018/023773, dated Sep. 18, 2018—2 pages.

* cited by examiner

*Primary Examiner* — Amanda Haney
(74) *Attorney, Agent, or Firm* — McCarter & English, LLP

(57) ABSTRACT

A therapeutic effect of irinotecan is predicted using a predetermined genetic polymorphism. A genetic polymorphism identified by rs1980576 in APCDD1L gene, or a genetic polymorphism in linkage disequilibrium with the above genetic polymorphism is analyzed, and determination is performed based on the genotype of the genetic polymorphism.

2 Claims, 5 Drawing Sheets

Specification includes a Sequence Listing.

Fig. 1

|   |   | Efficacy |   |   | P value |   | Odds ratio |
|---|---|---|---|---|---|---|---|
|   |   | Yes | No | (% of Yes) | Fisher* | C.-A.** | (Fisher*) |
| a) | *APCDD1L*; rs1980576 (A>G): ALTERNATIVE OF rs3946003 BASED ON WES ANALYSIS | | | | | | A/A vs A/G, G/G |
|   | A/A | 21 | 35 | (37.5) | 0.035 | 0.027 | $P = 0.191$  OR = 0.59 |
|   | A/G | 21 | 46 | (31.3) | | | A/A, A/G vs G/G |
|   | G/G | 1 | 16 | (5.9) | | | $P = 0.022$  OR = 0.12 |
| b) | *R3HCC1*; rs2272761 (G>A): LINKAGE TO rs13530 IN WES ANALYSIS | | | | | | G/G vs G/A, A/A |
|   | G/G | 4 | 6 | (40.0) | 0.733 | 0.506 | $P = 0.496$  OR = 0.65 |
|   | G/A | 13 | 28 | (31.7) | | | G/G, G/A vs A/A |
|   | A/A | 26 | 63 | (29.2) | | | $P = 0.704$  OR = 0.83 |
| c) | *OR5I2*; rs12577167 (A>G) | | | | | | A/A vs A/G, G/G |
|   | A/A | 22 | 48 | (31.4) | 0.329 | 0.673 | $P = 1.000$  OR = 0.94 |
|   | A/G | 15 | 42 | (26.3) | | | A/A, A/G vs G/G |
|   | G/G | 6 | 7 | (46.2) | | | $P = 0.219$  OR = 2.07 |
| d) | *MKKS*; rs1547 (C>T): LINKAGE TO rs1545 IN WES ANALYSIS | | | | | | C/C vs C/T, T/T |
|   | C/C | 21 | 47 | (30.9) | 0.653 | 0.732 | $P = 1.000$  OR = 0.98 |
|   | C/T | 17 | 43 | (28.3) | | | C/C, C/T vs T/T |
|   | T/T | 5 | 7 | (41.7) | | | $P = 0.513$  OR = 1.68 |
| e) | *EDEM3*; rs9425343 (T>G) | | | | | | T/T vs T/G, G/G |
|   | T/T | 11 | 25 | (30.6) | 0.971 | 0.798 | $P = 1.000$  OR = 1.01 |
|   | T/G | 20 | 48 | (29.4) | | | T/T, T/G vs G/G |
|   | G/G | 12 | 24 | (33.3) | | | $P = 1.000$  OR = 0.96 |
| f) | *APCDD1L*; rs7265854 (A>G) | | | | | | |
|   | A/A | 16 | 33 | (32.7) | 0.644 | 0.425 | |
|   | A/G | 22 | 46 | (32.4) | | | |
|   | G/G | 5 | 18 | (21.7) | | | |
|   | SEX | | | | | | |
|   | Male | 27 | 62 | (30.3) | 1.000 | - | |
|   | Female | 16 | 35 | (31.4) | | | |
|   | Age | | | | | | |
|   | <65 | 23 | 51 | (31.1) | 1.000 | - | |
|   | =>65 | 20 | 46 | (30.3) | | | |

\*, Fisher's exact test. \*\*, Cochran-Armitage trend test.

Fig. 2

|   |   | Efficacy | | | P value | | Odds ratio |
|---|---|---|---|---|---|---|---|
|   |   | Yes | No | (% of Yes) | Fisher* | C.-A.** | (Fisher*) |
| g) | *UGT1A1\*6* | | | | | | |
|   | -/- | 29 | 75 | (27.9) | 0.294 | - | |
|   | -/*6 | 14 | 22 | (38.9) | | | |
|   | *6/*6 | - | - | | | | |
| h) | *UGT1A1\*60* | | | | | | |
|   | -/- | 25 | 52 | (32.5) | 0.235 | 0.278 | |
|   | -/*60 | 18 | 38 | (32.1) | | | |
|   | *60/*60 | 0 | 7 | (0.0) | | | |
| i) | *UGT1A7 (387T>G)* | | | | | | |
|   | T/T | 16 | 40 | (28.6) | 0.863 | 0.587 | |
|   | T/G | 22 | 48 | (31.4) | | | |
|   | G/G | 5 | 9 | (35.7) | | | |
| j) | *UGT1A7 (622T>C)* | | | | | | |
|   | T/T | 26 | 60 | (30.2) | 1.000 | 0.866 | |
|   | T/C | 16 | 35 | (31.4) | | | |
|   | C/C | 1 | 2 | (33.3) | | | |
| k) | *UGT1A9\*1b* | | | | | | |
|   | *1b/*1b | 5 | 9 | (35.7) | 0.640 | 0.768 | |
|   | -/*1b | 20 | 53 | (27.4) | | | |
|   | -/- | 18 | 35 | (34.0) | | | |

*, Fisher's exact test. **, Cochran-Armitage trend test.

Fig. 3

|   |   | Efficacy | | | P value | | Odds ratio |
|---|---|---|---|---|---|---|---|
|   |   | Yes | No | (% of Yes) | Fisher* | C.-A.** | (Fisher*) |
| a) | *APCDD1L*; rs1980576 (A>G): ALTERNATIVE OF rs3946003 BASED ON WES ANALYSIS | | | | | | A/A vs A/G, G/G |
|   | A/A | 9 | 12 | (42.9) | 0.025 | 0.030 | P = 0.278  OR = 0.55 |
|   | A/G | 13 | 21 | (38.2) | | | A/A, A/G vs G/G |
|   | G/G | 0 | 11 | (0.0) | | | P = 0.012  OR = 0.00 |
| b) | *R3HCC1*; rs2272761 (G>A): LINKAGE TO rs13530 IN WES ANALYSIS | | | | | | |
|   | G/G | 3 | 3 | (50.0) | 0.669 | 0.595 | |
|   | G/A | 5 | 12 | (29.4) | | | |
|   | A/A | 14 | 29 | (32.6) | | | |
| c) | *OR5I2*; rs12577167 (A>G) | | | | | | |
|   | A/A | 13 | 25 | (34.2) | 0.743 | 0.898 | |
|   | A/G | 6 | 14 | (30.0) | | | |
|   | G/G | 3 | 4 | (42.9) | | | |
| d) | *MKKS*; rs1547 (C>T): LINKAGE TO rs1545 IN WES ANALYSIS | | | | | | |
|   | C/C | 9 | 18 | (33.3) | 0.337 | 0.504 | |
|   | C/T | 9 | 23 | (28.1) | | | |
|   | T/T | 4 | 3 | (57.1) | | | |
| e) | *EDEM3*; rs9425343 (T>G) | | | | | | |
|   | T/T | 7 | 12 | (36.8) | 0.397 | 0.705 | |
|   | T/G | 9 | 25 | (26.5) | | | |
|   | G/G | 6 | 7 | (46.2) | | | |
| f) | *APCDD1L*; rs7265854 (A>G) | | | | | | |
|   | A/A | 8 | 18 | (30.8) | 0.936 | 0.798 | |
|   | A/G | 11 | 20 | (35.5) | | | |
|   | G/G | 3 | 6 | (33.3) | | | |
|   | SEX | | | | | | |
|   | Male | 15 | 28 | (34.9) | 0.789 | - | |
|   | Female | 7 | 16 | (30.4) | | | |
|   | Age | | | | | | |
|   | <65 | 12 | 23 | (34.3) | 1.000 | - | |
|   | =>65 | 10 | 21 | (32.3) | | | |

*, Fisher's exact test. **, Cochran-Armitage trend test.

Fig. 4

|  |  | Efficacy | | | P value | | Odds ratio |
|---|---|---|---|---|---|---|---|
|  |  | Yes | No | (% of Yes) | Fisher* | C.-A.** | (Fisher*) |
| g) | *UGT1A1*6* |  |  |  |  |  |  |
|  | -/- | 13 | 33 | (28.3) | 0.257 | - |  |
|  | -/*6 | 9 | 11 | (45.0) |  |  |  |
|  | *6/*6 | - | - |  |  |  |  |
| h) | *UGT1A1*60* |  |  |  |  |  |  |
|  | -/- | 13 | 25 | (34.2) | 0.403 | 0.475 |  |
|  | -/*60 | 9 | 15 | (37.5) |  |  |  |
|  | *60/*60 | 0 | 4 | (0.0) |  |  |  |
| i) | *UGT1A7 (387T>G)* |  |  |  |  |  |  |
|  | T/T | 9 | 15 | (37.5) | 0.878 | 0.697 |  |
|  | T/G | 10 | 23 | (30.3) |  |  |  |
|  | G/G | 3 | 6 | (33.3) |  |  |  |
| j) | *UGT1A7 (622T>C)* |  |  |  |  |  |  |
|  | T/T | 12 | 27 | (30.8) | 0.816 | 0.654 |  |
|  | T/C | 9 | 15 | (37.5) |  |  |  |
|  | C/C | 1 | 2 | (33.3) |  |  |  |
| k) | *UGT1A9*1b* |  |  |  |  |  |  |
|  | *1b/*1b | 3 | 6 | (33.3) | 0.633 | 0.519 |  |
|  | -/*1b | 9 | 23 | (28.1) |  |  |  |
|  | -/- | 10 | 15 | (40.0) |  |  |  |

*, Fisher's exact test. **, Cochran-Armitage trend test.

Fig. 5

| Rank (st. dif.) | | Toxicity | | | P value |
|---|---|---|---|---|---|
| | | Yes | No | (% of Yes) | C.-A.** |
| Rank_1 | *APCDD1L*; rs1980576 (A>G): ALTERNATIVE OF rs3946003 BASED ON EXOME ANALYSIS | | | | |
| (2.16) | A/A | 5 | 16 | (23.8) | 0.008 |
| | A/G | 16 | 20 | (44.4) | |
| | G/G | 8 | 3 | (72.7) | |
| Rank_2, 3 | *R3HCC1*; rs2272761 (G>A): LINKAGE TO rs13530 IN EXOME ANALYSIS | | | | |
| (1.98) | G/G | 0 | 6 | (0.0) | 0.049 |
| | G/A | 8 | 11 | (42.1) | |
| | A/A | 21 | 22 | (48.8) | |
| Rank_4 | *OR5I2*; rs12577167 (A>G) | | | | |
| (1.81) | A/A | 20 | 19 | (51.3) | 0.052 |
| | A/G | 8 | 14 | (36.4) | |
| | G/G | 1 | 6 | (14.3) | |
| Rank_5, 6 | *MKKS*; rs1547 (C>T): LINKAGE TO rs1545 IN EXOME ANALYSIS | | | | |
| (1.73) | C/C | 8 | 20 | (28.6) | 0.042 |
| | C/T | 16 | 16 | (50.0) | |
| | T/T | 5 | 3 | (62.5) | |
| Rank_7 | *CSMD2*; rs474474 (A>G) | | | | |
| (1.71) | A/A | 17 | 16 | (51.5) | 0.334 |
| | A/G | 8 | 18 | (30.8) | |
| | G/G | 4 | 5 | (44.4) | |
| Rank_8 | *EDEM3*; rs9425343 (T>G) | | | | |
| (1.71) | T/T | 12 | 8 | (60.0) | 0.032 |
| | T/G | 14 | 21 | (40.0) | |
| | G/G | 3 | 10 | (23.1) | |
| Rank_9 | *GATA2*; rs2335052 (G>A) | | | | |
| (1.71) | G/G | 16 | 14 | (53.3) | 0.188 |
| | G/A | 10 | 20 | (33.3) | |
| | A/A | 3 | 5 | (37.5) | |
| Rank_10 | *APCDD1L*; rs7265854 (A>G) | | | | |
| (1.50) | A/A | 13 | 13 | (50.0) | 0.083 |
| | A/G | 15 | 18 | (45.5) | |
| | G/G | 1 | 8 | (11.1) | |
| Rank_11 | *ACOX1*; rs1135640 (C>G)***: $N = 67$ | | | | |
| (1.38) | C/C | 6 | 3 | (66.7) | 0.018 |
| | C/G | 15 | 14 | (51.7) | |
| | G/G | 8 | 21 | (27.6) | |

**, Cochran-Armitage trend test.
***, IN EXOME (N = 15), LINKED TO TRIM65 (rs3760128), TRIM65 (rs7222757), OR FBF1 (rs2305913).

METHOD FOR PREDICTING THERAPEUTIC EFFECTS OF IRINOTECAN, AND KIT FOR SAME

TECHNICAL FIELD

The present invention relates to a method for predicting a therapeutic effect of irinotecan and a kit for the same.

BACKGROUND ART

Irinotecan (CPT-11) is an anticancer drug synthesized from camptothecin, which is an antitumor alkaloid derived from Cancer tree (*Camptotheca acuminata*), and is known to be useful for treating cancer such as lung cancer and metastatic colorectal cancer. Irinotecan is metabolized in the liver and converted to SN-38, which is an active metabolite, to show an antitumor activity. It is also reported that irinotecan inhibits topoisomerase, which is an enzyme that accelerates DNA replication, to show an excellent anticancer activity, but also has significant toxicity causing side effects, leukopenia and diarrhea.

A glucuronidation enzyme (UDP-glucuronosyltransferase: UGT) is an enzyme catalyzing a reaction of adding glucuronic acid to a drug, foreign substance, or endogenous substance, such as bilirubin, steroid hormone, or bile acid, and it is known that UGT1A1, which is one of genes encoding the enzyme, has a genetic polymorphism. The above-mentioned SN-38 is inactivated through a conjugation reaction by the UGT and is then excreted.

It has been reported that the UGT1A1 genetic polymorphism is involved in the development of a side effect from irinotecan (CPT-11) as an anticancer drug. That is, it has been reported that in an individual having a UGT1A1 genetic polymorphism causing a reduction in the UGT activity, a risk of severe side effects, such as leukopenia and extreme diarrhea, is increased. UGT1A1*28, which is one of UGT1A1 genetic polymorphisms, is a genetic polymorphism in which the TA sequence is repeated 7 times in the promoter region TATA-box, whereas the sequence is repeated 6 times in the wild-type (UGT1A1*1) occupying the majority. The difference due to the insertion of two nucleotides, T and A, decreases the expression level of the gene, resulting in a reduction in the UGT activity.

In addition, the UGT1A1 gene has at least nine isoforms, UGT1A1 and UGT1A3 to UGT1A10. Regarding also the respective isoforms, as in the above-described UGT1A1 gene, a variety of genetic polymorphisms are known. Some of these genetic polymorphisms affect the enzymatic activity of UGT and the expression level of the gene, and it has also been reported that some of them are involved in the development of side effect from irinotecan.

At the same time, a UGT1A1 genetic polymorphism diagnostic kit (US TWT) by an invader method has been implemented as a diagnostic tool for diagnosing side effects from irinotecan. However, such a method has problems of low accuracy of discrimination and high cost of analysis. In addition, Patent Literature 1 discloses a method for efficiently determining the UGT1A1*28 polymorphism by a hybridization method using a nucleic acid probe corresponding to the UGT1A1*28 polymorphism in the UGT1A1 gene. Furthermore, Patent Literature 2 discloses the results of search for a new factor relating to side effects from irinotecan not caused by UGT1A genetic polymorphism through comprehensive analysis (exome analysis) of genomes of patients grouped based on the clinical information (presence or absence of side effects from irinotecan) and UGT1A genetic polymorphism information. Patent Literature 2 has mentioned single nucleotide polymorphisms in APCDD1L gene, R3HCC1 gene, OR5I2 gene, MKKS gene, EDEM3 gene, and ACOX1 gene as factors that help prediction of the risk of side effects from irinotecan.

CITATION LIST

Patent Literature

Patent Literature 1: JP Patent Publication (Kokai) No. 2008-072913A
Patent Literature 2: WO2016/132736

SUMMARY OF INVENTION

Technical Problem

Incidentally, the genetic polymorphisms described above participate in prediction of the frequency of side effects from administration of irinotecan. However, no genetic polymorphism involved in the therapeutic effect of irinotecan is known, and the therapeutic effect by administration of irinotecan cannot be determined.

Accordingly, it is an object of the present invention to provide a method for predicting a therapeutic effect of irinotecan or a method for helping the determination of a therapeutic effect by identifying a genetic polymorphism involved in the therapeutic effect of irinotecan and using the genetic polymorphism.

Solution to Problem

The present inventors have intensively studied to solve the above problems, as a result found that among genetic polymorphisms related to side effects from irinotecan, a specific genetic polymorphism is related to the therapeutic effect of irinotecan, and accomplished the present invention. The present invention includes the followings.

(1) A method for determining a therapeutic effect of irinotecan, comprising: analyzing a genetic polymorphism identified by rs1980576 in APCDD1L gene present in a genome DNA in a biological sample collected from a subject, or a genetic polymorphism in linkage disequilibrium or genetic linkage with the above genetic polymorphism, to determine a genotype of the genetic polymorphism; and determining the therapeutic effect based on the determined genotype.

(2) The method according to aspect (1), wherein the genetic polymorphism identified by rs1980576 is a single nucleotide polymorphism of adenine in wild-type to guanine in mutant-type at position 186 in the nucleotide sequence of APCDD1L gene set forth in SEQ ID NO: 1.

(3) The method according to aspect (1), wherein when the genetic polymorphism identified by rs1980576 has a homozygote of wild-type, it is determined that irinotecan will have a high therapeutic effect; when the genetic polymorphism is a heterozygote of mutant-type and wild-type, it is determined that irinotecan will have a therapeutic effect; and when the genetic polymorphism has a homozygote of mutant-type, it is determined that irinotecan will have a low therapeutic effect.

(4) The method according to aspect (1), wherein the genetic polymorphism in a relationship of linkage disequilibrium with the genetic polymorphism identified by rs1980576 is a single nucleotide polymorphism identified by rs3946003.

(5) A probe set for determining a therapeutic effect of irinotecan, the set comprising an oligonucleotide that hybridizes, under a stringent condition, to a region of 5 to 50 consecutive nucleotides including a genetic polymorphism identified by rs1980576 in APCDD1L gene, or a genetic polymorphism in linkage disequilibrium or genetic linkage with the above genetic polymorphism.

(6) The probe set for determining a therapeutic effect according to aspect (5), wherein the region of 5 to 50 nucleotides includes position 186 in the nucleotide sequence of APCDD1L gene set forth in SEQ ID NO: 1.

(7) The probe set for determining a therapeutic effect according to aspect (5), comprising a wild-type probe corresponding to a wild-type in the genetic polymorphism identified by rs1980576 and a mutant-type probe corresponding to a mutant-type in the genetic polymorphism.

(8) The probe set for determining a therapeutic effect according to aspect (5), wherein the genetic polymorphism in a relationship of linkage disequilibrium with the genetic polymorphism identified by rs1980576 is a single nucleotide polymorphism identified by rs3946003.

The probe set for determining a therapeutic effect of irinotecan according to the present invention may be a kit for determining a therapeutic effect of irinotecan including: a primer that amplifies the region of 5 to 50 nucleotides contained in a specimen. That is, the kit according to the present invention may include a primer that specifically amplifies a region of 5 to 50 consecutive nucleotides including a genetic polymorphism identified by rs1980576 in APCDD1L gene, or a genetic polymorphism in linkage disequilibrium or genetic linkage with the above genetic polymorphism; and the probe set for determining a therapeutic effect that specifically hybridizes to the amplified region. In addition, the kit according to the present invention may include various reagents necessary for amplifying the region and/or various reagents necessary for specifically hybridizing the amplified region and the nucleic acid probes. Furthermore, a DNA chip for determining a therapeutic effect of irinotecan can be prepared by immobilizing the probe set for determining a therapeutic effect of irinotecan to a carrier.

The present specification includes the content as disclosed in JP Patent Publication No. 2017-122569, which is a priority document of the present application.

Advantageous Effects of Invention

According to the present invention, a therapeutic effect of irinotecan can be determined with high accuracy by a simple method, detection of a genetic polymorphism.

BRIEF DESCRIPTION OF DRAWINGS

FIG. 1 is a characteristic diagram showing the results of analysis on a relationship between single nucleotide polymorphisms a) to f) and irinotecan therapeutic effects in 140 Japanese colorectal cancer patients treated with a regimen including irinotecan (statistical analysis results in 140 cases excluding weight loss cases, UGT1A1*6 and *28, and compound heterogeneous).

FIG. 2 is a characteristic diagram showing the results of analysis on a relationship between single nucleotide polymorphisms g) to k) and irinotecan therapeutic effects in the same 140 cases in FIG. 1 (statistical analysis results in 140 cases excluding weight loss cases, UGT1A1*6 and *28, and compound heterogeneous).

FIG. 3 is a characteristic diagram showing the results of analysis on a relationship between single nucleotide polymorphisms a) to f) and irinotecan therapeutic effects in subpopulation, 66 cases, limited to FOLFIRI cases among the 140 cases.

FIG. 4 is a characteristic diagram showing the results of analysis on a relationship between single nucleotide polymorphisms g) to k) and irinotecan therapeutic effects in subpopulation, 66 cases, limited to FOLFIRI cases among the 140 cases.

FIG. 5 is a characteristic diagram showing the results of analysis on a relationship between single nucleotide polymorphisms and side effects from irinotecan described in Table 2 of WO2016/132736 (PCT/JP2016/000793) (statistical analysis results (N=68) in cases excluding UGT1A1*28 homo and *6 homo and compound hetero).

DESCRIPTION OF EMBODIMENTS

The present invention relates to a method for determining a therapeutic effect of irinotecan by identifying a genetic polymorphism identified by rs1980576 in APCDD1L gene, or a genetic polymorphism in linkage disequilibrium or genetic linkage with the above genetic polymorphism. Irinotecan: (S)-4,11-diethyl-3,4,12,14-tetrahydro-4-hydroxy-3,14-dioxo-1H-pyrano[3',4':6,7]indolizino[1,2-b]quinolin-9-yl ester, CPT-11, 1,4'-bipiperidine-1'-carboxylic acid (CAS NO: 97682-44-5) is a compound synthesized from camptothecin, which is an antitumor alkaloid derived from Cancer tree (*Camptotheca acuminata*). In the present invention, irinotecan encompasses its salts and their solvates, especially hydrates (e.g., CAS NO: 136572-09-3). As a salt of irinotecan, an acid addition salt prepared by reacting a pharmaceutically acceptable acid is preferably used as an anticancer drug. Examples of the acid addition salt include salts with inorganic acids such as hydrochloric acid, sulfuric acid, phosphoric acid, and hydrobromic acid; and salts with organic acids such as oxalic acid, maleic acid, fumaric acid, malic acid, tartaric acid, citric acid, benzoic acid, acetic acid, p-toluenesulfonic acid, and methanesulfonic acid. Especially, a hydrochloride (irinotecan hydrochloride, CAS NO: 136572-09-3) is preferably used.

Irinotecan is converted to an active metabolite SN-38 by a carboxyl esterase after in vivo administration. SN-38 is detoxified in the liver through a conjugation reaction with a glucuronidation enzyme (UDP-glucuronosyltransferase: UGT) and is then excreted to the intestinal tract. The adaptation disease of irinotecan is not particularly limited, and examples thereof include small cell lung cancer, non-small cell lung cancer, cervical cancer, ovarian cancer, gastric cancer (non-operable or recurrent), colorectal cancer (non-operable or recurrent), breast cancer (non-operable or recurrent), squamous cell cancer, malignant lymphoma (non-Hodgkin's lymphoma), childhood malignant solid tumor, and unresectable pancreatic cancer. That is, according to the present invention, it is possible to determine the therapeutic effect of irinotecan on the above-mentioned respective cancer.

In the identification of the genetic polymorphism, a genome DNA contained in a biological sample collected from a subject can be used. Here, the biological sample to be collected from a subject may be any sample containing a genome DNA, and examples thereof include body fluids, such as blood and blood-related samples derived blood (e.g., blood, serum, and plasma), lymph, sweat, tears, saliva, urine, feces, ascites, and cerebrospinal fluid; and cell, tissue, or organ homogenates and extracts. In the present invention, a blood-related sample is preferably used.

The genome DNA may be extracted from a biological sample collected from a subject by any method and is preferably extracted by a method that can separate, purify, and collect a DNA component directly from the biological sample.

Here, the nucleotide sequence of APCDD1L gene (NCBI Accession No: NM_153360.1, Last updated: Jan. 26, 2014) is set forth in SEQ ID NO: 1. The genetic polymorphism identified by rs1980576 in APCDD1L gene is located at position 186 of the nucleotide sequence set forth in SEQ ID NO: 1. The genetic polymorphism identified by rs1980576 (i.e., the nucleotide at position 186 of the nucleotide sequence set forth in SEQ ID NO: 1) is adenine in the wild-type and is guanine in the mutant-type. In a complementary strand of the nucleotide sequence of APCDD1L gene set forth in SEQ ID NO: 1, the nucleotide is thymine in the wild-type and is cytosine in the mutant-type.

"Linkage disequilibrium" means a population-genetic phenomenon that there is a non-random correlation between alleles of multiple gene loci or genetic markers (polymorphisms) in a population of organisms, that is, the frequency of such a specific combination (haplotype) significantly increases. "Genetic linkage" means a genetic phenomenon that a specific combination of alleles is inherited from a parent to a child without obeying Mendel's law of independence. Specifically, the genetic polymorphism in linkage disequilibrium or genetic linkage with the genetic polymorphism identified by rs1980576 is not particularly limited, and examples thereof include a single nucleotide polymorphism identified by rs3946003.

As the method for identifying the genetic polymorphism, i.e., the method for typing the genetic polymorphism, a known method for analyzing a single nucleotide polymorphism can be used, and examples of the method include a real-time PCR method, a direct sequencing method, a TaqMan® PCR method, an Invader® method, a Luminex® method, a quenching primer/probe (QP) method, an MALDI-TOF method, and a molecular beacon method. Specifically, the method is, for example, a method by amplifying a nucleic acid fragment containing a single nucleotide polymorphism site as a measurement object using primers by an amplification reaction using a genome DNA in a biological sample collected from a subject (usually refers to a human subject) as a template and detecting hybridization of the resulting nucleic acid fragment and a pair of probes corresponding to a wild-type and a mutant-type or a method for detecting a wild-type and a mutant-type by using a probe specific to the single nucleotide polymorphism site in the PCR amplification process.

The probe set used in the identification of a genetic polymorphism (i.e., a probe set for determining a therapeutic effect of irinotecan) may be any probe set including an oligonucleotide that hybridizes to a region of 5 to 50 consecutive nucleotides, preferably 10 to 40 nucleotides, and more preferably 15 to 30 nucleotides containing the genetic polymorphism identified by rs1980576 under a stringent condition. In addition, in use of an oligo probe synthesized using an artificial nucleic acid, such as a locked nucleic acid (LNA), as a probe, even a short nucleotide sequence can also be used as the probe for specific hybridization. The term "probe set" means a wild-type probe corresponding to the wild-type allele and a mutant-type probe corresponding to the mutant-type allele. As an example, the nucleotide sequence of a wild-type probe is set forth in SEQ ID NO: 2, and the nucleotide sequence of a mutant-type probe is set forth in SEQ ID NO: 3.

The stringent condition refers to a condition in which a so-called specific hybrid is formed and non-specific hybrid is not formed. Specifically, an example thereof is a condition under which a hybrid is formed at 45° C. in a solution containing 6×SSC (a solution containing 1.5 M NaCl and 0.15 M trisodium citrate is defined as 10×SSC) and 50% formamide and is then washed with 2×SSC at 50° C. In addition, the stringent condition can be appropriately set in accordance with 6.3.1-6.3.6 in Molecular Biology, John Wiley & Sons, N.Y. (1989). Alternatively, an example of the stringent condition is a condition under which a hybrid is formed at 54° C. in a solution containing 3×SSC and 0.3×SDS and is then washed with washing solution A (10×SSC and 1% SDS solution), washing solution B (20× SSC), and then washing solution C (5×SSC) sequentially (see JP Patent Publication (Kokai) No. 2011-250726A).

In addition, the probe set used in the identification of a genetic polymorphism may be used by immobilized on a carrier. Examples of the carrier include a planar substrate and a bead-like spherical carrier, specifically, the carrier described in JP Patent Publication (Kokai) No. 2011-250726A. In addition, a probe for detecting a wild-type and a probe for detecting a mutant-type may be immobilized on a single carrier or may be immobilized on different carriers.

The primer used in the method for identifying a genetic polymorphism may be any primer including oligonucleotides that can amplify at least consecutive five nucleotides containing a genetic polymorphism identified by rs1980576 as a nucleic acid fragment by using a genome DNA as a template. More specifically, a primer including oligonucleotides that can amplify at least 5 nucleotides, preferably 10 to 500 nucleotides, more preferably 20 to 200 nucleotides, and further preferably 50 to 100 nucleotides containing the nucleotide at position 186 in the nucleotide sequence of APCDD1L gene set forth in SEQ ID NO: 1 can be appropriately designed based on the nucleotide sequence set forth in SEQ ID NO: 1.

When at least consecutive five nucleotides containing a genetic polymorphism identified by rs1980576 is amplified, the amplified sequence can be identified by using a primer labeled in advance or using a labeled nucleotide as a substrate in the amplification reaction. The labeling material is not particularly limited, and examples thereof include radioisotopes, fluorescent dyes, and organic compounds such as digoxigenin (DIG) and biotin.

The probe or primer can be prepared by, for example, chemical synthesis with an apparatus for synthesizing nucleic acid. As the nucleic acid-synthesizing apparatus, for example, a DNA synthesizer or a fully automated nucleic acid synthesizer can be used.

When an amplified nucleic acid fragment has a label, the nucleic acid fragment hybridized to a probe (the wild-type probe or the mutant-type probe included in the probe set for determining a therapeutic effect of irinotecan) can be measured by detecting the label. For example, when a fluorescent dye is used as the label, the nucleic acid fragment hybridized to the probe can be measured by measuring the fluorescent intensity caused by the fluorescent dye. Specifically, the ratio of the nucleic acid fragment hybridized to the wild-type probe and the nucleic acid fragment hybridized to the mutant-type probe can be calculated from the output value in the detection of the label in the wild-type probe and the output value in the detection of the label in the mutant-type probe. When a fluorescent label is used as the label, the output value is the fluorescent intensity.

More specifically, the determination value can be calculated by dividing the output value (fluorescent intensity) derived from the nucleic acid fragment hybridized to a mutant-type probe by the average value of the output value (fluorescent intensity) derived from the nucleic acid fragment hybridized to the mutant-type probe and the output value (fluorescent intensity) derived from the nucleic acid fragment hybridized to a wild-type probe. The determination value approximates to a value obtained by normalizing the amount of the mutant-type present in the nucleic acid fragment. Accordingly, it is possible by the level of the determination value to analyze a single nucleotide polymorphism in a subject and discriminate whether the polymorphism has a homozygote of mutant-type, a homozygote of wild-type, or a heterozygote.

When the determination value is used, in order to analyze a single nucleotide polymorphism in a subject and discriminate whether the polymorphism has a homozygote of mutant-type, a homozygote of wild-type, or a heterozygote, it is preferable to previously set two-step thresholds (threshold A and threshold B). Here, threshold A and threshold B have a relationship: threshold A>threshold B. That is, when the determination value calculated as described above is higher than threshold A, it is determined that the polymorphism has a homozygote of mutant-type; when the determination value is not higher than threshold A and higher than threshold B, it is determined that the polymorphism has a heterozygote; and when the determination value is not higher than threshold B, it is determined that the polymorphism has a homozygote of wild-type.

Threshold A and threshold B may be set by any method and may be set by, for example, calculating determination values as described above using samples of which the genotypes are previously discriminated and calculating the respective probability densities when having a homozygote of mutant-type, when having a homozygote of wild-type, or when having a heterozygote as normal distributions. On this occasion, an intersection at which the probability densities overlap (the position where the magnitudes of the probability densities are replaced with each other between the respective maximum values) is determined, and the respective average values when having a homozygote of mutant-type, when having a homozygote of wild-type, and when having a heterozygote are determined. The thresholds when having a homozygote of mutant-type and when having a heterozygote can be calculated as the average value of (the average value when having a homozygote of mutant-type and the average value when having a heterozygote) and the average value of intersections. Similarly, the thresholds when having a heterozygote and when having a homozygote of wild-type can be calculated as the average value of (the average value when having a heterozygote and the average value when having a homozygote of wild-type) and the average value of intersections.

Regarding a subject, when the genetic polymorphism identified by rs1980576 has a homozygote of wild-type, it is determined that irinotecan will have a high therapeutic effect; when the genetic polymorphism has a heterozygote of mutant-type and wild-type, it is determined that irinotecan will have a therapeutic effect; and when the genetic polymorphism has a homozygote of mutant-type, it is determined that irinotecan will have a low therapeutic effect. Here, the subject as a determination object is, for example, an individual who is suspected of having a disease in the above-mentioned application range of irinotecan or an individual having such a disease, and is not particularly limited.

EXAMPLES

The present invention will now be described in detail by Examples, but the technical scope of the present invention is not limited to the following Examples.

Example 1

(Analysis Object)

Analysis objects were 140 cases among 155 Japanese colorectal cancer (stage IV) cases who were administered with irinotecan excluding cases who were administered with a reduced amount of irinotecan, UGT1A1*6 (homo), UGT1A1*28 (homo), and their compound heterogeneous cases and determined for the therapeutic effect and 66 subpopulation cases (FOLFIRI cases with a unified regimen) among the 140 cases. FOLFIRI is one of standard treatments for colorectal cancer and using irinotecan simultaneous with treatment with a combination of fluorouracil and 1-leucovorin. The 140 cases were Japanese colorectal cancer patients treated with a regimen including irinotecan. The regimen in this Example includes combination therapy, in addition to irinotecan, with FOLFIRI using fluorouracil and 1-leucovorin, XELIRI using capecitabine, IRIS using S-1, or an anti-EGFR antibody agent (Bevacizumab, Cetuximab, or Panitumumab).

(Preparation of Genome DNA)

A genome DNA was prepared from each case by the following method. Collected peripheral blood was added to an EDTA-containing tube. Subsequently, a DNA was prepared based on a sodium iodide method (Wang, et al., Nucleic Acids Res., 34: 195-201 (2014)). The prepared DNA was dissolved in 10 mM Tris-hydrochloric acid buffer (pH 8.0) containing 1 mM EDTA·2Na and was stored at 4° C. or −20° C. until use.

(Genetic Polymorphism Analysis)

Comprehensive analysis (WES analysis) of the prepared genome DNA was performed by the same method as described in WO2016/132736 (PCT/JP2016/000793). That is, three types of cases: cases (n=5) as a control group in which UGT1A genetic polymorphisms (seven positions of UGT1A1*6, *27, and *28, UGT1A7 (387T>G and 622T>C), UGT1A9*1b, and UGT1A1*60) were all homozygotes being low in side effect risk and no side effect from irinotecan were observed; cases (n=5) as a case group in which although the UGT1A genetic polymorphisms were the same as those in the control group, side effects (Grade 3, entire course) were observed; and cases (n=5) in which any of the UGT1A genetic polymorphisms was a heterozygote and a side effect was observed from the first administration of irinotecan (Grade 4), were established, and the case and control groups were analyzed. As validation, genotyping using a hydrolysis probe was performed. The genetic polymorphisms and the side effect frequency and the response rates were statistically analyzed using a Cochran-Armitage trend test.

From the WES analysis results, the differences in the allele frequency between the control group and the case group were ranked using a standardized difference. Correlation of high-ranked polymorphisms with frequency of hematotoxicity (Grade 3 or higher), which is a side effect from irinotecan, was analyzed for 155 cases using a TaqMan hydrolysis probe. On this occasion, although single nucleotide polymorphisms in APCDD1L gene identified by WES analysis were rs3946003 and rs7265854 in consideration of influence on amino acid sequences, primers and probes for rs3946003 could not be designed by the method using a TaqMan hydrolysis probe. Accordingly, rs1980576 not influencing the amino acid sequence but completely linked to rs3946003 in WES analysis was used as an alternative object of rs3946003. As a result, a significant linear trend with side effect frequency was observed in a) a single nucleotide polymorphism rs1980576 in APCDD1L gene, b) a single nucleotide polymorphism rs2272761 in R3HCC1 gene, c) a single nucleotide polymorphism rs12577167 in OR5I2 gene, d) a single nucleotide polymorphism rs1547 in MKKS gene, e) a single nucleotide polymorphism rs9425343 in EDEM3 gene, and f) a single nucleotide polymorphism rs7265854 in APCDD1L gene.

Here, it is generally thought that when a side effect is high, the effect of the agent is strong, that is, the therapeutic effect is high. Accordingly, 11 single nucleotide polymorphisms in total: the above-mentioned single nucleotide polymorphisms a) to f) and single nucleotide polymorphisms g) UGT1A1*6, h) UGT1A1*60, i) UGT1A7 (387T>G), j) UGT1A7 (622T>C), and k) UGT1A9*1b known to be involved in side effects from irinotecan, were analyzed for a relationship with the therapeutic effects of irinotecan on cancer. The therapeutic effects of irinotecan on cancer were evaluated based on RECIST (response criteria for solid tumors) to CR (complete response, complete disappearance of target lesion), PR (partial response, at least 30% reduction in the sum of diameters of target lesion compared to the sum of diameters at baseline), SD (stable disease, no tumor regression corresponding to PR and tumor progression corresponding to PD are recognized), or PD (progressive disease, at least 20% increase in the sum of diameters of target lesion compared to the minimum sum of diameters, and an increase of at least 5 mm as the absolute value). CR and PR were determined to have a therapeutic effect; and SD and PD were determined to have no therapeutic effect.

The relationships between the respective single nucleotide polymorphisms and the therapeutic effect of irinotecan are shown in FIGS. 1 to 4. FIGS. 1 and 2 show the analysis results of 140 cases determined for therapeutic effects, and FIGS. 3 and 4 show the analysis results of 66 subpopulation cases among the 140 cases. In the P values in FIGS. 1 to 4, "C.-A." indicates the results of Cochran-Armitage trend test, and "Fisher" indicates the results of Fisher's exact test. In addition, in FIGS. 1 to 4, "Odds ratio" is calculated as an odds ratio of the therapeutic effects (efficacy) of irinotecan on cancer in a wild-type homozygote or a mutant-type homozygote by Fisher's exact test.

As shown in FIGS. 1 to 4, in the single nucleotide morphisms b) to k) among the single nucleotide polymorphisms a) to k), no relationships between the respective single nucleotide polymorphisms and the therapeutic effects of irinotecan on cancer were observed. On the other hand, in the single nucleotide polymorphism a), rs1980576, in APCDD1L gene, the C.-A. values were 0.027 and 0.030 in FIGS. 1 and 3, respectively, and a significant linear trend was observed between the single nucleotide polymorphism rs1980576 in APCDD1L gene and the therapeutic effects of irinotecan on cancer.

As described in WO2016/132736 (PCT/JP2016/000793), only the risk of side effects from irinotecan has been predicted by the single nucleotide polymorphism rs1980576 of APCDD1L gene. However, according to this Example, it has been revealed that the single nucleotide polymorphism rs1980576 can predict the risk of side effects from irinotecan and also the therapeutic effect of irinotecan on cancer.

In addition, according to examination in combination with the content of FIG. 5, which is described in Table 2 of WO2016/132736 (PCT/JP2016/000793), it is possible to predict that when the single nucleotide polymorphism rs1980576 has a wild-type homozygote (A/A), there is a possibility of a therapeutic effect of irinotecan on cancer, and the risk of side effects is low and that when the single nucleotide polymorphism rs1980576 has a heterozygote (A/G), the possibility of a therapeutic effect of irinotecan on cancer is high, and the risk of side effects is low. Considering that the response rate of irinotecan is generally about 32%, it is possible to determine that when the single nucleotide polymorphism rs1980576 has a wild-type homozygote (A/A), the therapeutic effect was observed in 38% in FIG. 1 and in 43% in FIG. 3 showing only FOLFIRI cases, and administration of irinotecan is effective especially in FOLFIRI therapy.

On the other hand, it is possible to predict that when the single nucleotide polymorphism rs1980576 has a mutant-type homozygote (G/G), there is no therapeutic effect on cancer, and the risk of side effects is high. In such a case, it is possible to perform a therapy suitable for a patient by examining other methods for treating the cancer before starting treatment by administration of irinotecan.

Since the side effects from irinotecan are caused by the prolonged retention of the active form in the body due to delayed detoxification of irinotecan, it is assumed that if the side effects are high, the therapeutic effect may also be high. According to this approach, it is predicted that when the single nucleotide polymorphism rs1980576 is a mutant-type homozygote (G/G), the risk of side effects is high, and the therapeutic effect is high. However, according to this Example, contrary to such general understanding, when the single nucleotide polymorphism rs1980576 is a mutant-type homozygote (G/G), the therapeutic effect is low, which is an unexpected result. Such a result is probably caused by that the single nucleotide polymorphism rs1980576 of APCDDL1 gene is involved in the risk of side effects from irinotecan but is not involved in the metabolism of irinotecan.

In addition, as shown in FIG. 1 of WO2016/132736 (PCT/JP2016/000793), since the single nucleotide polymorphism rs1980576 and the single nucleotide polymorphism rs3946003 are in a relationship of linkage disequilibrium, it is possible to predict a therapeutic effect of irinotecan on cancer by determining the genotype of the single nucleotide polymorphism rs3946003.

All publications, patents, and patent applications cited in the present specification are hereby incorporated by reference in their entirety.

The invention claimed is:

1. A method for determining a therapeutic effect of irinotecan, comprising:
   (a) isolating genomic DNA from a biological sample collected from a subject;
   (b) analyzing the isolated genomic DNA to detect the genotype of SNP rs1980576 in the APCDD1L gene;
   (c) determining the therapeutic effect based on the detected genotype,
   wherein when (i) AA is at rs1980576, it is determined that irinotecan will have a high therapeutic effect; (ii) AG is at rs1980576 is detected, it is determined that irinotecan will have a therapeutic effect; and (iii) GG is at rs1980576 is detected, it is determined that irinotecan will have a low therapeutic effect; and
   (d) administering irinotecan to the subject when AA or AG is at rs1980576 or administering a cancer treatment other than irinotecan to the subject when GG is at rs1980576.

2. The method according to claim 1, wherein SNP rs1980576 results in an adenine to guanine change at position 186 of SEQ ID NO: 1.

* * * * *

SEQUENCE LISTING

<160> NUMBER OF SEQ ID NOS: 3

<210> SEQ ID NO 1
<211> LENGTH: 1506

<212> TYPE: DNA
<213> ORGANISM: Homo sapiens

<400> SEQUENCE: 1

| | | | | | | |
|---|---|---|---|---|---|---|
| atgcccgcag | ccatgctccc | ctacgcttgc | gtcctggtgc | ttttgggagc | ccacactgca | 60 |
| ccggcggctg | gggaggccgg | gggcagctgc | ctgcgctggg | aaccccactg | ccagcagccc | 120 |
| ttgccagata | gagtgcccag | cactgcgatc | ctgcctccac | gccttaatgg | accttggatc | 180 |
| tccacaggct | gcgaggtgcg | cccaggaccg | gagttcctga | cccgcgccta | caccttctac | 240 |
| cccagccggc | tctttcgagc | ccaccagttc | tactacgagg | acccccttctg | cggggaacct | 300 |
| gcccactcgc | tgctcgtcaa | gggcaaagtc | cgcctgcgcc | gggcctcctg | ggtcacccgg | 360 |
| ggagccaccg | aggccgacta | ccacctgcac | aaggtgggca | tcgtcttcca | cagccgccgg | 420 |
| gccctggtcg | acgtcaccgg | gcgcctcaac | cagacccgcg | ccggccggga | ctgcgcgcgg | 480 |
| cggctgcctc | cggcccgggc | ctggctgcct | ggggcgctgt | acgagctgcg | gagcgcccgg | 540 |
| gctcaggggg | actgcctgga | ggcgctgggc | ctcaccatgc | acgagctcag | cctggtccgc | 600 |
| gtgcagcgcc | gcctgcagcc | gcagcccgg | gcgtcgcccc | ggctggtgga | ggagctgtac | 660 |
| ctgggggaca | tccacaccga | cccggcggag | aggcggcact | accggcccac | gggctaccag | 720 |
| cgcccgctgc | agagcgcact | gcaccacgtg | cagccgtgcc | cagcctgtgg | cctcattgcc | 780 |
| cgctccgatg | tgcaccaccc | gcccgtgctg | ccgcccccctc | tggccctgcc | cctgcacctg | 840 |
| ggcggctggt | gggtcagctc | ggggtgcgag | gtgcgcccag | cagtcctgtt | cctcacccgg | 900 |
| ctcttcactt | tccacgggca | cagccgctcc | tgggaagggt | attaccacca | cttctcagac | 960 |
| ccagcctgcc | ggcagcccac | cttcaccgtg | tatgccgccg | gccgctacac | caggggcacg | 1020 |
| ccatccacca | gggtccgcgg | cggcaccgag | ctggtgtttg | aggtcacacg | ggcccatgtg | 1080 |
| acccccatgg | accaggtcac | cacggccatg | ctcaacttct | ctgagccaag | cagctgtggg | 1140 |
| ggtgcggggg | cctggtccat | gggcactgag | cgggatgtca | cagccaccaa | cggctgccta | 1200 |
| ccgctgggca | tccggctccc | gcatgtggag | tacgagcttt | tcaagatgga | caagaccccc | 1260 |
| ctcgggcaaa | gcctgctctt | catcggacaa | aggcccaccg | atggctcaag | tcccgatacc | 1320 |
| ccagagaaac | gtcccacctc | ctaccaagca | cccctggtgc | tctgtcatgg | ggaggccccc | 1380 |
| gacttctcca | ggccaccgca | gcacaggcca | tcgctgcaga | agcaccccag | cacaggggt | 1440 |
| cttcacatag | ccccttccc | acttctgccc | ctagttctag | ggctggcctt | cctccactgg | 1500 |
| ctatga | | | | | | 1506 |

<210> SEQ ID NO 2
<211> LENGTH: 51
<212> TYPE: DNA
<213> ORGANISM: Artificial
<220> FEATURE:
<223> OTHER INFORMATION: Synthetic DNA

<400> SEQUENCE: 2
gtcaggatga cctgaagtct taccctgtgg agatccaagg tccattaagg c          51

<210> SEQ ID NO 3
<211> LENGTH: 51
<212> TYPE: DNA

-continued

```
<213> ORGANISM: Artificial
<220> FEATURE:
<223> OTHER INFORMATION: Synthetic DNA

<400> SEQUENCE: 3
gtcaggatga cctgaagtct taccccgtgg agatccaagg tccattaagg c            51
```